(12) United States Patent
Boyd

(10) Patent No.: US 10,500,083 B1
(45) Date of Patent: Dec. 10, 2019

(54) METHOD OF USING AN INTRAORAL DISCLUDER TO ENHANCE MIGRAINE PREVENTION AND TREATMENT OF TEMPOROMANDIBULAR DISORDERS

(71) Applicant: James Palmer Boyd, Rancho Santa Fe, CA (US)

(72) Inventor: James Palmer Boyd, Rancho Santa Fe, CA (US)

( * ) Notice: Subject to any disclaimer, the term of this patent is extended or adjusted under 35 U.S.C. 154(b) by 428 days.

(21) Appl. No.: 15/491,824

(22) Filed: Apr. 19, 2017

Related U.S. Application Data

(60) Provisional application No. 62/324,628, filed on Apr. 19, 2016.

(51) Int. Cl.
*A61F 5/058* (2006.01)

(52) U.S. Cl.
CPC ................ *A61F 5/05891* (2013.01)

(58) Field of Classification Search
CPC .. A61F 5/05891; A61F 5/56; A61F 2005/563; A61F 5/566; A61F 5/58
See application file for complete search history.

(56) References Cited

U.S. PATENT DOCUMENTS

| 6,666,212 B2 * | 12/2003 | Boyd, Sr. | A61C 7/36 128/859 |
| 7,654,267 B2 * | 2/2010 | Boyd | A61F 5/566 128/859 |

* cited by examiner

*Primary Examiner* — Tarla R Patel
(74) *Attorney, Agent, or Firm* — Plager Schack LLP; Mark H. Plager; Eric Liou

(57) ABSTRACT

A method to enhance migraine prevention and treatment of temporomandibular disorders with use of an intraoral discluder device includes providing the intraoral discluder device. The intraoral discluder device has a trough with a front wall and a rear wall designed to accommodate at least one maxillary incisor or mandibular incisor of the user, and a protrusion coupled to the trough. The method further includes maneuvering the intraoral discluder device in the user to accommodate the at least one maxillary incisor to permit the protrusion to contact at least one mandibular incisor of the lower jaw during a bite of the user, determining the spacing between the maxillary molars and mandibular molars, and ensuring the spacing between the maxillary molars and mandibular molars is no greater than approximately 2 millimeters during the bite.

6 Claims, 3 Drawing Sheets

METHOD OF USING AN INTRAORAL DISCLUDER TO ENHANCE MIGRAINE PREVENTION AND TREATMENT OF TEMPOROMANDIBULAR DISORDERS

RELATED APPLICATION

The application claims priority to provisional patent application U.S. Ser. No. 62/324,628 filed on Apr. 19, 2016, the entire contents of which is herein incorporated by reference.

BACKGROUND

The embodiments herein relate generally to an insightful improvement in the protocol in the use of an intraoral discluder device for use in preventing migraine headaches and the treatment of temporomandibular disorders.

Research on migraines has helped to develop a better understanding of the causes of these headaches and treatment options. As stated in the Indian Academy of Neurology ("Ann Indian Acad Neurol. 2012 August; 15 (Suppl 1): S15-S22.), " Migraine is a form of sensory processing disturbance with wide ramifications for central nervous system function, and while pain is used as the exemplar symptom, a brain-centered explanation provides a framework to understand all the manifestations of migraine . . . there is a form of central sensitization that may be classical central sensitization, or a form of dysinhibitory sensitization with dysfunction of descending modulatory pathways. Interestingly, the presence or absence of allodynia does not predict outcome from acute therapy in randomized controlled trials."

Current medical prophylaxis for chronic migraine therefore is to limit or block all noxious efferents to the trigeminal sensory nucleus, with the intent of limiting central sensitization, as a sensitized trigeminal sensory nucleus is most susceptible to producing migraine attacks upon being stimulated.

U.S. Pat. No. 6,666,212 discloses an intraoral discluder device and method for preventing migraine and temporomandibular disorders. However, the understanding of the use of the intraoral discluder mistakenly assumes that muscle fatigue or spasm is a source of migraine pain when actually it is now best considered as a major contributing noxious input to the trigeminal sensory nucleus, thereby being a source of negative influence on central sensitization. In current on-going medical trials observing the use of the intraoral discluder compared to placebo devices, several patients have reported an increase in migraine frequency and pain with the discluder.

Further examination of these patients revealed two major oversights in migraine prevention that might have produced an unintended increase in central sensitization. First, the selection of a discluding device to be used on the maxillary incisors cannot be one of convenience for the provider. Practitioners commonly elect to provide a discluding device on the patient's maxillary teeth primarily because of the ease of fabrication and delivery, as the mandibular incisors are commonly less than ideally aligned, thereby making a discluding device on the mandibular incisors far more time consuming and complicated. However, the use of a maxillary device can allow for an opposing mandibular canine tooth to contact the maxillary retained device when the patient moves their mandible in an extreme right or left excursive from centered. A mandibular canine tooth contact on a maxillary-placed discluder device can allow for near maximal clenching intensity (Becker, JProsDent, July 1999, vol 82), thereby eliciting considerable noxious input, resulting in an increase in migraine frequency and intensity.

Second, providing a discluding device on either arch without addressing the thickness of the device and allowing it to be excessive between the maxillary and mandibular incisors can result in an excessive rotation of the mandibular condyle in a static position while clenching, that is, "over opened" during clenching events on the discluding device. In normal mastication, the rotation of the condyle is minimal during intense crushing of objects. If the thickness of the discluding device causes an excessive degree of rotation during clenching on the discluding device ("over opened"), the jaw joint can be strained, eliciting considerable noxious input, thereby increasing migraine frequency and intensity.

As such, there is a need in the industry for a method of using an intraoral discluder device that addresses the limitations of the prior art, which enhances migraine prevention and the treatment of temporomandibular disorders.

SUMMARY

A method to enhance migraine prevention and treatment of temporomandibular disorders with use of an intraoral discluder device is provided. The method is configured to minimize detrimental use of the intraoral discluder device maxillary or mandibularly retained by a user. The method comprises administering to the user the intraoral discluder device, the intraoral discluder device comprising a trough comprising a first longitudinal axis, a front wall and a rear wall configured to accommodate at least one maxillary incisor or mandibular incisor of the user, and a protrusion coupled to the trough and comprising a second longitudinal axis generally perpendicular to the first longitudinal axis, the protrusion projecting anteriorly from the front wall of the trough and posteriorly from the front wall to the rear wall beneath a bottom portion of the trough. The method further comprises maneuvering the intraoral discluder device in the user to permit the front and rear walls to accommodate the at least one maxillary incisor and determining the spacing between the maxillary molars and mandibular molars during a bite on the intraoral discluder device.

In certain embodiments of the invention, the method further comprises ensuring the spacing between the maxillary molars and mandibular molars is no greater than approximately 2 millimeters. In certain embodiments of the invention, the method further comprises observing the spacing between the maxillary molars and mandibular molars to be greater than approximately 2 millimeters, and performing an adjustment on the discluder device to reduce a thickness of the discluder device until the spacing between the maxillary molars and mandibular molars is no greater than approximately 2 millimeters during the bite of the user.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
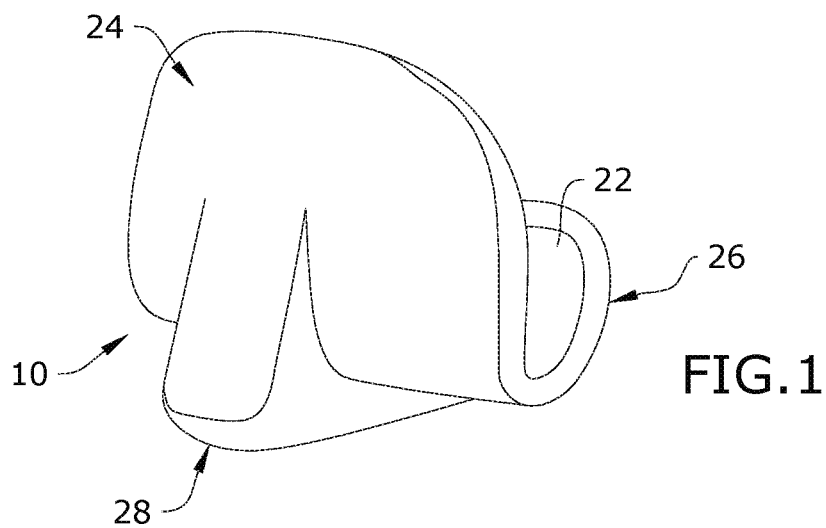
FIG. 1 depicts a perspective view of an intraoral discluder device used in certain embodiments of the invention.

As depicted in FIG. 1, an exemplary intraoral discluder 10 is configured for use in a user's mouth and comprises trough 22 defined by front wall 24 and rear wall 26. Trough 22 comprises a first longitudinal axis. Protrusion 28 is coupled to trough 22 and comprises a second longitudinal axis generally perpendicular to the first longitudinal axis. Protrusion 28 projects anteriorly from front wall 24 of trough 22 and posteriorly from front wall 24 to rear wall 26 beneath a bottom portion of the trough. Space between front wall 24 and rear wall 26 of intraoral discluder 10 is configured to accommodate at least one maxillary incisor or mandibular incisor of the user as will become apparent in the remaining figures and accompanying description. Intraoral discluder 10 may be made from any biocompatible material such as polycarbonates, polymers, enamels, rubbers, silicone resins, or the like.

It shall be appreciated that properly sized discluder 9, improperly sized discluder 11, maxillary retained discluder 15 and mandibularly retained discluder 16 depicted in FIGS. 3-7 are the same as intraoral discluder 10. However, intraoral discluders with alternative structural components may be used instead.

FIGS. 2-7 depict the anatomy of the user, which comprises mandible 1 known as the lower jaw and maxilla 5 known as the upper jaw. Mandible 1 comprises a plurality of teeth comprising at least one mandibular molar 7, at least one mandibular incisor 13 and at least one mandibular canine tooth 14. Typically, the user comprises a plurality of mandibular molars 7, a plurality of mandibular incisors 13 and a pair of mandibular canine teeth 14. Mandible 1 further comprises condyle 3, which is positioned proximate temporal bone 2 of the user's skull. Maxilla 5 comprises a plurality of teeth comprising maxillary molars 6 and at least one maxillary incisor 17. Typically, the user comprises a plurality of maxillary molars 6 and a plurality of maxillary incisors 17.

Figure 2:
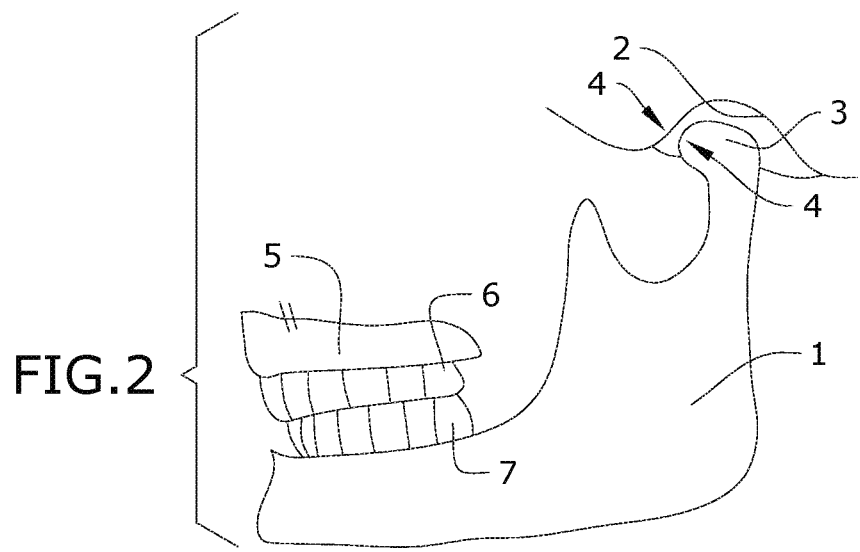
FIG. 2 depicts a side schematic view of certain embodiments of the invention without use of the intraoral discluder device.

FIG. 2 depicts the user during a normal bite or jaw clenching. In this position, mandible 1 is elevated so that maxillary molars 6 and mandibular molars 7 are pressed together. This results in tolerable static spacing 4 between temporal bone 2 and condyle 3.

Figure 3:
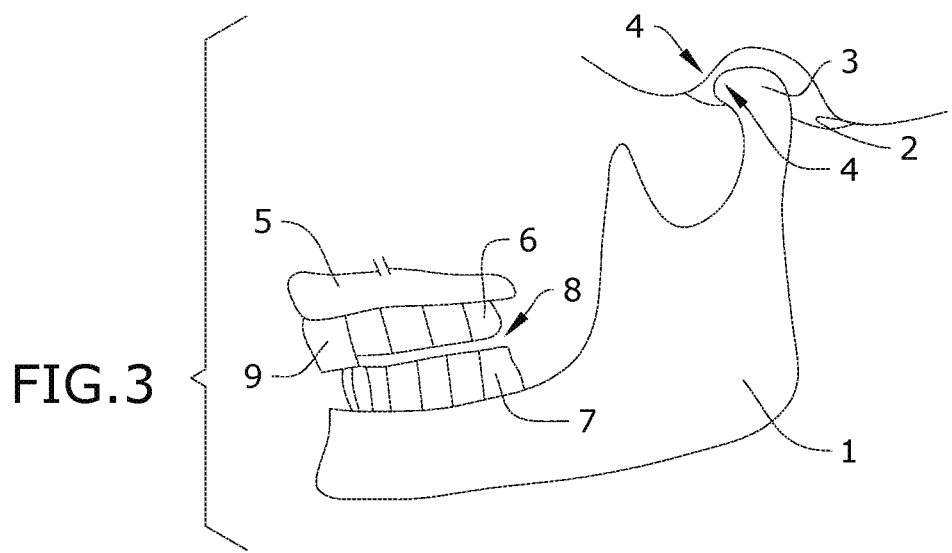
FIG. 3 depicts a side schematic view of certain embodiments of the invention illustrating the intraoral discluder device shown in use.
Figure 4:
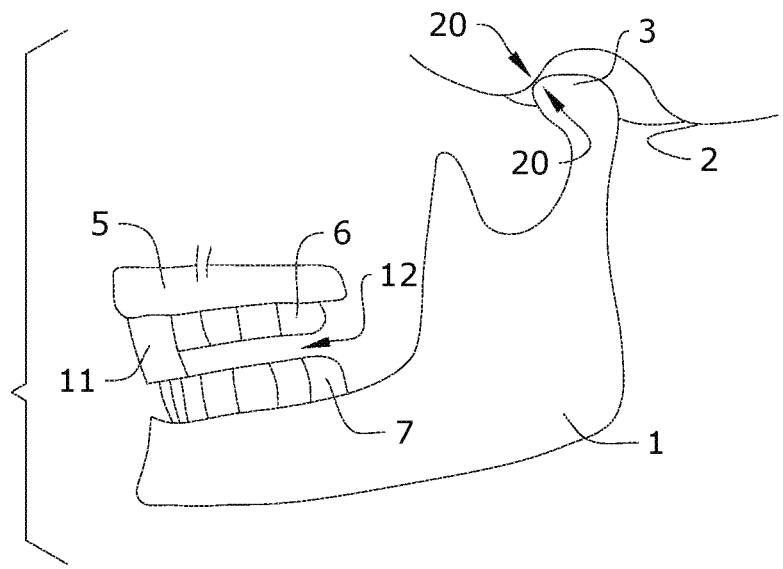
FIG. 4 depicts a side schematic view of certain embodiments of the invention illustrating the intraoral discluder device shown in use.

FIGS. 3-4 depict the use of intraoral discluders in the user's mouth. During the use of an intraoral discluder, it is beneficial for the freeway space between opposing maxillary and mandibular molars to be no greater than 2 millimeters when the user bites on the discluder. This freeway space ensures a lack of excessive rotation of condyle 3 during clenching events on the discluder, thereby minimizing detrimental use of the intraoral discluder and likelihood of increased migraine frequency of the user.

FIG. 3 depicts the use of properly sized discluder 9 maxillary retained in the user's mouth. In this position, proper freeway space 8 exists between maxillary molars 6 and mandibular molars 7 of approximately 2 millimeters or less when the user bites on properly sized discluder 9. This creates tolerable static spacing 4 between temporal bone 2 and condyle 3, and a lack of excessive rotation of condyle 3 during clenching or biting events on the discluder. Therefore, the detrimental use of the intraoral discluder and likelihood of increased migraine frequency of the user is minimized.

FIG. 4 depicts the use of improperly sized discluder 11 maxillary retained in the user's mouth. In this position, excessive freeway space 12 between maxillary molars 6 and mandibular molars 7 of more than 2 millimeters exists. This causes excessive rotation of condyle 3 during clenching or biting events on the discluder, which creates intolerable static spacing 20 between temporal bone 2 and condyle 3. As a result, the detrimental use of the intraoral discluder and likelihood of increased migraine frequency of the user is not minimized.

Figure 5:
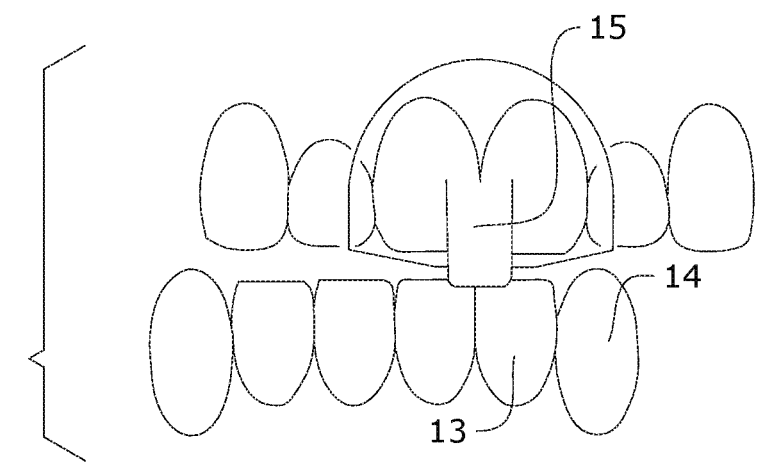
FIG. 5 depicts a front schematic view of certain embodiments of the invention illustrating the intraoral discluder device shown in use.
Figure 6:
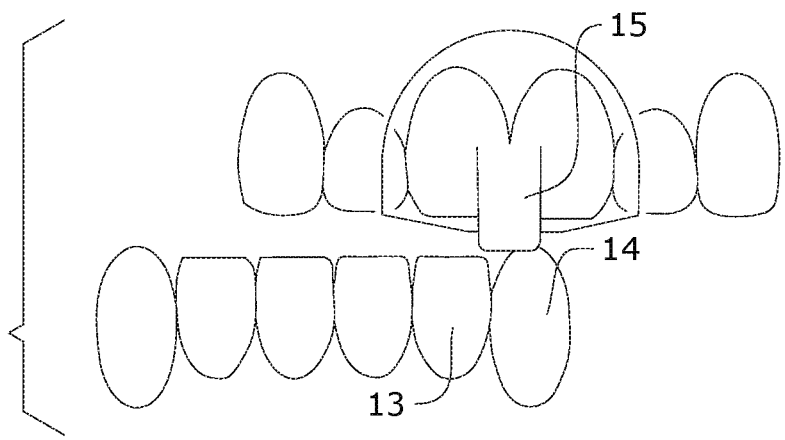
FIG. 6 depicts a front schematic view of certain embodiments of the invention illustrating the intraoral discluder device shown in use.

FIGS. 5-6 depict the use of maxillary retained discluder 15 in the user's mouth. During an acceptable use, maxillary retained discluder 15 contacts at least one mandibular incisor 13 during lateral left or right mandibular movements as depicted in FIG. 5. However, certain users may engage in extreme lateral left or right mandibular movements, which causes maxillary retained discluder 15 to contact at least one mandibular canine tooth 14 as depicted in FIG. 6.

Figure 7:
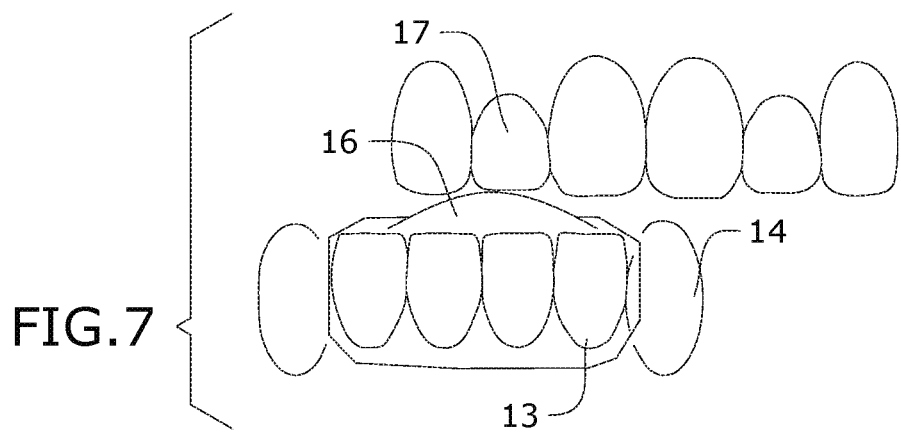
FIG. 7 depicts a front schematic view of certain embodiments of the invention illustrating the intraoral discluder device shown in use.

The contact between maxillary retained discluder 15 and mandibular canine tooth 14 may result in maximum clenching intensity, which results in an increase in migraine intensity and/or frequency. Under these circumstances, maxillary retained discluder 15 should be removed and secured to at least one mandibular incisor 13 to reduce clenching intensity. FIG. 7 depicts mandibularly retained discluder 16, which contacts at least one maxillary incisor 17 when the user bites on the discluder.

In operation of intraoral discluder 10, one or more of the following exemplary steps are performed. It shall be appreciated that the addition or removal of certain steps are entirely possible and within the scope of embodiments of the invention.

First, a practitioner maneuvers intraoral discluder 10 in the user to permit front and rear walls 24, 26 to accommodate at least one maxillary incisor 17. This permits protrusion 28 to contact at least one mandibular incisor 13 of the lower jaw during a bite of the user. The practitioner checks to ensure in extreme right or left mandibular movements, that neither of mandibular canine 14 can contact intraoral discluder 10 when maxillary retained. If there is no contact between mandibular canine 14 and intraoral discluder 10, the discluder can be maxillary retained. If there is contact between mandibular canine 14 and intraoral discluder 10 in this excursive position, intraoral discluder 10 has to be adapted to be mandibularly retained as shown in FIG. 7.

Regardless of whether intraoral discluder 10 is maxillary or mandibularly retained, the practitioner must check to ensure that no greater than approximately 2 millimeters of space exists between maxillary molars 6 and mandibular molars 7. If the spacing between maxillary molars 6 and mandibular molars 7 is observed to be greater than approximately 2 millimeters, the practitioner performs an adjustment on intraoral discluder 10 to reduce the thickness of the device until spacing between maxillary molars 6 and mandibular molars 7 is no greater than approximately 2 millimeters during the bite of the user. The practitioner may use any variety of methods and tools to grind or reduce the thickness of intraoral discluder 10 to the desired size.

It shall be appreciated that the components of the intraoral discluder described in several embodiments herein may comprise any alternative known materials in the field and be of any color, size and/or dimensions. It shall be appreciated that the components of the intraoral discluder described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A method to enhance migraine prevention and treatment of temporomandibular disorders with use of an intraoral discluder device, the method configured to minimize detrimental use of the intraoral discluder device maxillary or mandibularly retained by a user, the user comprising an upper jaw comprising maxillary incisors, maxillary canines and maxillary molars, and a lower jaw comprising mandibular incisors, mandibular canines and mandibular molars, the method comprising:

administering to the user the intraoral discluder device, the intraoral discluder device comprising:

a trough comprising a first longitudinal axis, a front wall and a rear wall configured to accommodate at least one maxillary incisor or mandibular incisor of the user; and a protrusion coupled to the trough and comprising a second longitudinal axis generally perpendicular to the first longitudinal axis, the protrusion projecting anteriorly from the front wall of the trough and posteriorly from the front wall to the rear wall beneath a bottom portion of the trough;

maneuvering the intraoral discluder device in the user to permit the front and rear walls to accommodate the at least one maxillary incisor, thereby permitting the protrusion to contact at least one mandibular incisor of the lower jaw during a bite of the user to maintain spacing between the maxillary molars and mandibular molars; and determining the spacing between the maxillary molars and mandibular molars ensuring the spacing between the maxillary molars and mandibular molars is no greater than approximately 2 millimeters.

2. The method of claim 1, further comprising observing the spacing between the maxillary molars and mandibular molars to be greater than approximately 2 millimeters, and performing an adjustment on the discluder device to reduce a thickness of the discluder device until the spacing between the maxillary molars and mandibular molars is no greater than approximately 2 millimeters during the bite of the user.

3. The method of claim 1, further comprising determining whether the discluder device contacts at least one mandibular canine of the user when the upper jaw or lower jaw is in an excursive position.

4. The method of claim 3, further comprising observing contact between the discluder device and at least one mandibular canine of the user in the excursive position and maneuvering the discluder device in the user to permit the front and rear walls to accommodate the at least one mandibular incisor of the user, thereby permitting the protrusion of the discluder device to contact at least one maxillary incisor of the upper jaw during another bite of the user to maintain spacing between the maxillary molars and mandibular molars.

5. The method of claim 4, further comprising ensuring the spacing between the maxillary molars and mandibular molars is no greater than approximately 2 millimeters.

6. The method of claim 4, further comprising observing the spacing between the maxillary molars and mandibular molars to be greater than approximately 2 millimeters, and performing an adjustment on the discluder device to reduce a thickness of the discluder device until the spacing between the maxillary molars and mandibular molars is no greater than approximately 2 millimeters during the another bite of the user.

\* \* \* \* \*